United States Patent
Berci et al.

(10) Patent No.: US 7,044,909 B2
(45) Date of Patent: *May 16, 2006

(54) VIDEO LARYNGOSCOPE WITH DETACHABLE LIGHT AND IMAGE GUIDES

(75) Inventors: George Berci, Los Angeles, CA (US); Marshal B. Kaplan, Beverly Hills, CA (US); James P. Barry, Charlton, MA (US); David Chatenever, Santa Barbara, CA (US); Klaus M. Irion, Liptingen (DE); Andre Ehrhardt, Wurmlingen (DE); Jurgen Rudischhauser, Tuttlingen (DE); Daniel Mattsson-Boze, Sacramento, CA (US)

(73) Assignee: Karl Storz GmbH & Co. KG, (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/068,600

(22) Filed: Feb. 28, 2005

(65) Prior Publication Data

US 2005/0148821 A1 Jul. 7, 2005

Related U.S. Application Data

(63) Continuation of application No. 10/285,190, filed on Oct. 31, 2002, now Pat. No. 6,890,298, which is a continuation-in-part of application No. 09/418,542, filed on Oct. 14, 1999, now Pat. No. 6,494,826.

(51) Int. Cl.
*A61B 1/267* (2006.01)

(52) U.S. Cl. .............. 600/185; 600/188; 600/194; 600/213

(58) Field of Classification Search ............ 600/112, 600/117, 118, 130–132, 156, 121, 185, 188, 600/194, 213
See application file for complete search history.

(56) References Cited

U.S. PATENT DOCUMENTS

| | | | |
|---|---|---|---|
| 3,986,854 A | 10/1976 | Scrivo et al. |
| 4,402,313 A | 9/1983 | Yabe |
| 4,565,187 A | 1/1986 | Soloway |
| 4,611,888 A | 9/1986 | Prenovitz et al. |
| 4,807,594 A | 2/1989 | Chatenever |
| 4,846,153 A | 7/1989 | Berci |
| 4,901,142 A | 2/1990 | Ikuno et al. |
| 5,101,807 A | 4/1992 | Kawashima |
| 5,125,394 A | 6/1992 | Chatenever et al. |
| 5,193,135 A | 3/1993 | Miyagi |
| 5,239,983 A | 8/1993 | Katsurada |
| 5,261,392 A | 11/1993 | Wu |
| 5,307,804 A | 5/1994 | Bonnet |

(Continued)

FOREIGN PATENT DOCUMENTS

CH    650342 A5    9/1985

(Continued)

OTHER PUBLICATIONS

New Tech, "Flexiscope Multivision", Schmitt, Maucher & Borjes.

(Continued)

*Primary Examiner*—Beverly M. Flanagan
(74) *Attorney, Agent, or Firm*—St. Onge Steward Johnston & Reens LLC

(57) ABSTRACT

A combination laryngoscope and video display for providing images of the area ahead of the laryngoscope to facilitate insertion without damaging the surrounding tissue; the laryngoscope having a detachable blade and a rigid, detachable light and image guide attachment device for providing illuminating light ahead of the blade and for detecting the reflected light.

15 Claims, 4 Drawing Sheets

U.S. PATENT DOCUMENTS

| | | |
|---|---|---|
| 5,311,859 A | 5/1994 | Monroe et al. |
| 5,329,936 A | 7/1994 | Lafferty et al. |
| 5,498,230 A | 3/1996 | Adair |
| 5,591,119 A | 1/1997 | Adair |
| 5,667,475 A | 9/1997 | Laser et al. |
| 5,682,199 A | 10/1997 | Lankford |
| 5,751,340 A | 5/1998 | Strobel et al. |
| 5,827,178 A | 10/1998 | Berall |
| 5,879,289 A | 3/1999 | Yarush et al. |

FOREIGN PATENT DOCUMENTS

| | | |
|---|---|---|
| DE | 4002812 A1 | 8/1990 |
| DE | 3914825 C1 | 9/1990 |
| DE | 4445599 A1 | 9/1995 |
| DE | 29506789 U1 | 10/1995 |
| DE | 19715510 A1 | 10/1998 |
| EP | 0501088 A1 | 12/1991 |

OTHER PUBLICATIONS

The Role of the Universal Video Intubating System In The Management Of The Difficult Airway, Berci, Chhibber, Kaplan, Van De Wiele and Ward, Jul. 2001.

VIDEO LARYNGOSCOPE WITH DETACHABLE LIGHT AND IMAGE GUIDES

PRIORITY DOCUMENT

The present application is a continuation application of U.S. patent application Ser. No. 10/285,190, filed Oct. 31, 2002, now U.S. Pat. No. 6,890,298 which is a continuation-in-part of U.S. patent application 09/41 8,542, filed Oct. 14, 1999 now U.S. Pat. No. 6,494,826,

FIELD OF THE INVENTION

The invention relates to an intubating video laryngoscope with a rigid, detachably connectable light guiding system and video guiding system.

BACKGROUND OF THE INVENTION

In the United States, approximately 10 million patients are operated on and anesthetized each year. While anesthetized, the patient's breathing functions are temporarily disabled. Ventilation is therefore supplied to the patient by the anesthesiologist during the procedure.

Ventilation is provided through an endotracheal tube. This tube is inserted into the trachea, and it is closed against the wall of the trachea by an inflatable cuff. The insertion of this tube involves risks that the anesthesiologist seeks to avoid or at least minimize. It is estimated that between one in 6,000 to one in 8,000 general anesthesia procedures result in death. There are of course many causes but of these it is estimated that about one third of them are caused by the intubation procedure.

The foremost obstacles encountered by the anesthesiologist include; the remoteness of the location where the tube is to be positioned, the consequent restriction of view as the tube is inserted, variations and anomalies in the anatomy of the patients, an uncomfortable and unnatural position for the anesthesiologist while holding the instrument, the potential need to change blades during the procedure, and the necessity for rapid intubation.

It should be noted that when the tube is inserted, the patient is asleep hyperoxygenated and then paralyzed for the procedure, and therefore not breathing. In addition, the ventilator is not yet in operation. This gives the anesthesiologist only about two minutes in which to intubate the patient, inflate the cuff, and start ventilation. If he is delayed because of unsuccessful attempts, he must stop, apply a ventilation mask to the patient, supply oxygen for a time through the mask, remove the mask, adjust medication if necessary, and then start over again. This delays the operation and extends the patient's time under anesthesia. This extension of time while under anesthesia may have very serious consequences, especially for elderly patients.

With the advent of endoscopic equipment and small cameras, instrumentation has been improved to the extent that it can enable viewing of the cords and larynx on a video screen thereby facilitating the intubation of the patient in a relatively quick and safe manner. However, conventional instrumentation may be further improved such that the laryngoscope is easier to use, thereby reducing the time involved for instance, to change blades or attach and detach peripheral components.

Endoscopes are now widely used in minimally invasive surgery. Endoscopes typically contain a light guiding system, usually in the form of fiber optic cables, in order to bring light to the surgical area. The light guiding system typically extends through the handle of the laryngoscope and through a guide tube located in the blade so as to position the light guiding system to illuminate the area ahead of the blade. Endoscopes also typically contain an image guiding system, for example in the form of a rigid rod lens system, arranged in the shaft of the endoscope. The image guiding system can also be configured as an ordered, flexible fiber optic bundle. The image guiding system is utilized to transmit reflected light from the area ahead of the blade to a camera. The camera, attached at the proximal end of the endoscope, usually contains a CCD (charge coupled device) sensor, in the form of a light-sensitive chip that converts the optical signals into electrical signals that are conveyed from the image-sensing camera module to a remotely located image processing system. The image guide typically extends from the distal end of the blade through the guide tube and then through the handle of the laryngoscope.

Typically, the combination light guiding system and image guiding system are permanently attached to the handle and are continuous, extending from the distal end of the blade, through the handle of the laryngoscope and to the camera for the image guiding system, and to the light source for the light guiding system. Therefore, the light guiding system and image guiding system extending from the handle of the laryngoscope for insertion into the guide tube of the blade typically comprise flexible coherent fiber optic bundles. However, when changing blades, the bundle must be carefully inserted or withdrawn from the opening of the guide tube at the proximal end of the blade. This may take an unacceptable amount time for the physician to thread the bundle into the tube if the blade must be changed in the middle of the intubation process.

The light and image guiding systems have typically been permanently attached to the handle to ensure the system will reliably transmit the illuminating light and reflected images. To utilize a detachably connectable light and image guiding system, the attachment means would have to rigidly hold the member in place such that the light and image guiding systems did not become misaligned. In addition, the attachment means must be easy and quick to operate, making it possible to perform the coupling procedure with as little close attention as possible, but nevertheless reliably. Provision must therefore be made for the coupling elements to be keyed to each other so that the coupling cannot be incorrectly joined and so that close attention by the operation is not required.

In addition, the flexible bundles may easily be damaged and will wear over time, degrading or rendering the system inoperable. As a visual inspection of the device often will not indicate whether the bundles are damaged, it is conceivable that a physician may obtain a damaged or malfunctioning laryngoscope not realizing that it is damaged. The time involved with determining that the instrument is malfunctioning, withdrawing it, finding another laryngoscope, and then intubating the patient may have severe adverse effects upon the patient under anesthesia.

Further, laryngoscopes, as with most medical equipment, must be sterilized after use. Because the light and image guiding systems are permanently attached to the handle, they are exposed to extremely high temperatures, which also cause wear and/or failure of the flexible bundles. Also, because the light and image guiding systems are subjected to the sterilization process with the handle and blades, the handle must be hermetically sealed which may greatly add to the cost in manufacturing such a device.

It is therefore desired to provide an improved video laryngoscope that is easy to use and will facilitate the quick removal and reattachment of a blade, the light guiding system and the image guiding system.

It is also desired to provide an improved video laryngoscope with a highly durable light guiding system and image guiding system.

It is further desired to provide an improved video laryngoscope that will reduce the costs associated with the manufacture of the laryngoscope.

It is also desired to provide an improved video laryngoscope having a coupling system that will reliably connect the laryngoscope handle with a light and image guiding attachment while requiring a minimal amount of attention from the user to attach or detach.

SUMMARY OF THE INVENTION

These and other objectives are achieved by providing a video laryngoscope having a coupling mechanism that connects the laryngoscope handle to the blade and light and image guide.

Accordingly, the coupling mechanism is provided with a first cylindrical stem of specific diameter and specific length, in whose interior is received a proximal end segment of the light guiding system, and which projects from one coupling end of the light and image guide in the coupling direction. Further, a second cylindrical stem is provided whose length and diameter are greater than the length and diameter of the first stem, having a proximal end segment of the image guiding system being received in the interior of the second stem, and which projects from one coupling end of the light and image guide in the coupling direction. The second stem coacts with an interlock system arranged in the laryngoscope handle forming a rigid mechanical coupling, the first and second stems extending at a distance next to one another. Complementary receptacles corresponding to the two stems, into which the stems penetrate, are provided in the laryngoscope handle. The base of the receptacle into which the second stem penetrates is optically connected to the camera, and the receptacle in which the shorter first stem is receivable is connected to the light source.

The mechanical, light-guiding, and image-guiding coupling is accomplished by way of a single simple linear displacement operation, in which specifically the two stems are pushed into the corresponding receptacles of the laryngoscope handle. Because one of the two stems is thicker and longer than the other, incorrect (i.e. reversed) insertion is not possible. Because the thicker stem is also simultaneously the longer one, it is possible, without undue attention, to feel for the correspondingly larger receptacle on the camera module with this thicker and longer stem, and then to close the coupling with an insertion movement. Incorrect attachment is thus no longer possible, since the thicker and longer stem cannot be attached to the smaller-diameter receptacle for the smaller and shorter stem.

The mechanical interlock or coupling is affected simultaneously with this insertion. Because the larger stem is also the longer stem, and it carries the image guiding system, the image-guiding connection occurs at an axial spacing from the light-guiding connection. This feature has the advantage that any stray light that might emerge from the light connection cannot directly come into contact with the image-guiding connecting point located at an axial distance therefrom. The disadvantages of connecting image and light at the same level, or those, for example, of a coaxial arrangement, are thus eliminated.

Because the coupling mechanism is keyed, the physician can therefore, for example, sense the laryngoscope handle and its precise grasped position in the coupling region with one hand, and with the other hand can easily sense the light and image guiding attachment and its grasped position as well, so that the two elements to be coupled can then be inserted into one another without visual contact. This greatly facilitates handling, especially when, during a procedure, one blade needs to be quickly exchanged for another, such that the light and image guiding attachment must be removed and re-attached along with the blade.

An interlock system is displaceable transversely to the coupling direction that can be engaged into a recess on the second stem. This feature has the advantage that in order to close and/or release the coupling, the locking element is displaced transversely to the coupling direction and is engaged into or disengaged from the recess on the second stem. These are all procedures that can be controlled, without visual contact, with the fingers of one hand; the snapping of the locking element into and out of the recess on the stem indicates to the operator whether the coupling is closed or open. If the locking element needs to be pushed into the recess, for example to close the coupling, this can be done by simply inserting the stems into their corresponding receptacles; precise locking can be ascertained by an audible sound that the locking element has been engaged. The locking element may comprise for instance, ball catches, hooks, snap lugs, or the like.

The locking element is acted upon by the force of a spring, and radially projects into the receptacle for the second stem. This is advantageous because, the force of the spring presses the locking element into a defined position, and the coupling may be disengaged by the application of a force opposite the coupling direction, namely withdrawing the stems from their respective receptacles. These are all procedures that can be sensed and controlled with the hand's sense of touch, so that no visual attention or observation is necessary when closing and opening the coupling.

The second stem may have a conical segment at the end that is followed by an undercut. The conical segment constitutes an insertion aid upon insertion of the stem into the receptacle, so that exact insertion is guaranteed with even approximate placement. At the same time, the conical surface can be utilized to displace the locking element radially upon insertion.

In addition, the undercut in the second stem may be configured as an annular groove. This forms a relatively large engagement surface with the locking element, so that the mechanical forces acting on the coupling will be dispersed over the entire area, which contributes to mechanical stability and less wear through use.

In addition, the first and second stems along with the receptacles receiving them each have a window. The windows thereby provide a sealed closure for the light and image guiding systems.

The light and image guide may in one advantageous embodiment be provided with a stainless steel outer casing, or some other suitable enclosure, for protecting the light and image guides. As the light and image guide is detachable from the handle, the handle does not have to be hermetically sealed for sterilization. Rather, only the light and image guide need be subjected to sterilization with the blade.

Accordingly, in one advantageous embodiment of the present invention, an intubating laryngoscope system is provided comprising a blade, a handle and a joinder for detachably connecting the handle to the blade. The system also includes a two-stem receptacle connector, a first light guide for transmitting illuminating light that is terminated in the two-stem receptacle connector, an first image guide for transmitting reflected light that is also terminated in the two-stem receptacle connector, and a light and image guiding attachment, detachably connectable to the handle. The light and image guiding attachment includes a two-stem plug connector designed to mate with the two-stem receptacle connector, a second light guide for transmitting illuminating light and terminated in the two-stem plug connector, a second image guide for transmitting reflected light and terminated in the two-stem plug connector, and a substantially rigid outer casing for encasing the second light guide and the second image guide.

In another advantageous embodiment of the present invention, an intubating laryngoscope system is provided comprising a handle having first light guide and a first image guide, a blade, a joinder for detachably connecting the handle to the blade, and a receptacle connector for terminating the first light guide and the first image guide. The system further includes a light and image guiding attachment that is detachably connectable to the handle and has a plug connector with a first stem and a second stem, a second light guide terminated in the first stem, a second image guide terminated in the second stem, and a substantially rigid outer casing for encasing the second light guide and the second image guide.

In yet another advantageous embodiment of the present invention, a method for providing an intubating laryngoscope system is disclosed including the steps of providing a handle having a first light guide and a first image guide, providing a blade, providing a first connector associated with the handle, terminating the first light guide and the first image guide in the first connector, and providing a light and image guide that is detachably connectable to the handle. The light and image guide have having a second light guide and a second image guide located therein. The method further includes terminating the second light guide in a second connector, terminating the second image guide in the second connector, detachably connecting the blade to the handle, and detachably connecting the light and image guide to the handle via the first and second connectors In addition, the light and image guide containing the second light and image guides may or may not be detachably connectable with the blade.

In still another advantageous embodiment of the present invention, an intubating laryngoscope is provided comprising a handle having a first light guide and a second image guide associated therewith, a blade connected to the handle, a first connector for terminating the first light guide and the first image guide, and a second light and image guide associated with the blade The second light and image guides connectable with the first light and image guides associated with the handle, and a second connector engageable with the first connector, a the second light guide terminated in the second connector, and a the second image guide terminated in the second connector. In addition, the first light guide and the first image guide are in communication with the second light guide and the second image guide respectively, via the first and second connectors.

It is understood that the features mentioned above and those yet to be explained below can be used not only in the respective combinations indicted, but also in other combinations or by themselves, without leaving the context of the present invention.

DETAILED DESCRIPTION OF THE DRAWINGS

Figure 1:
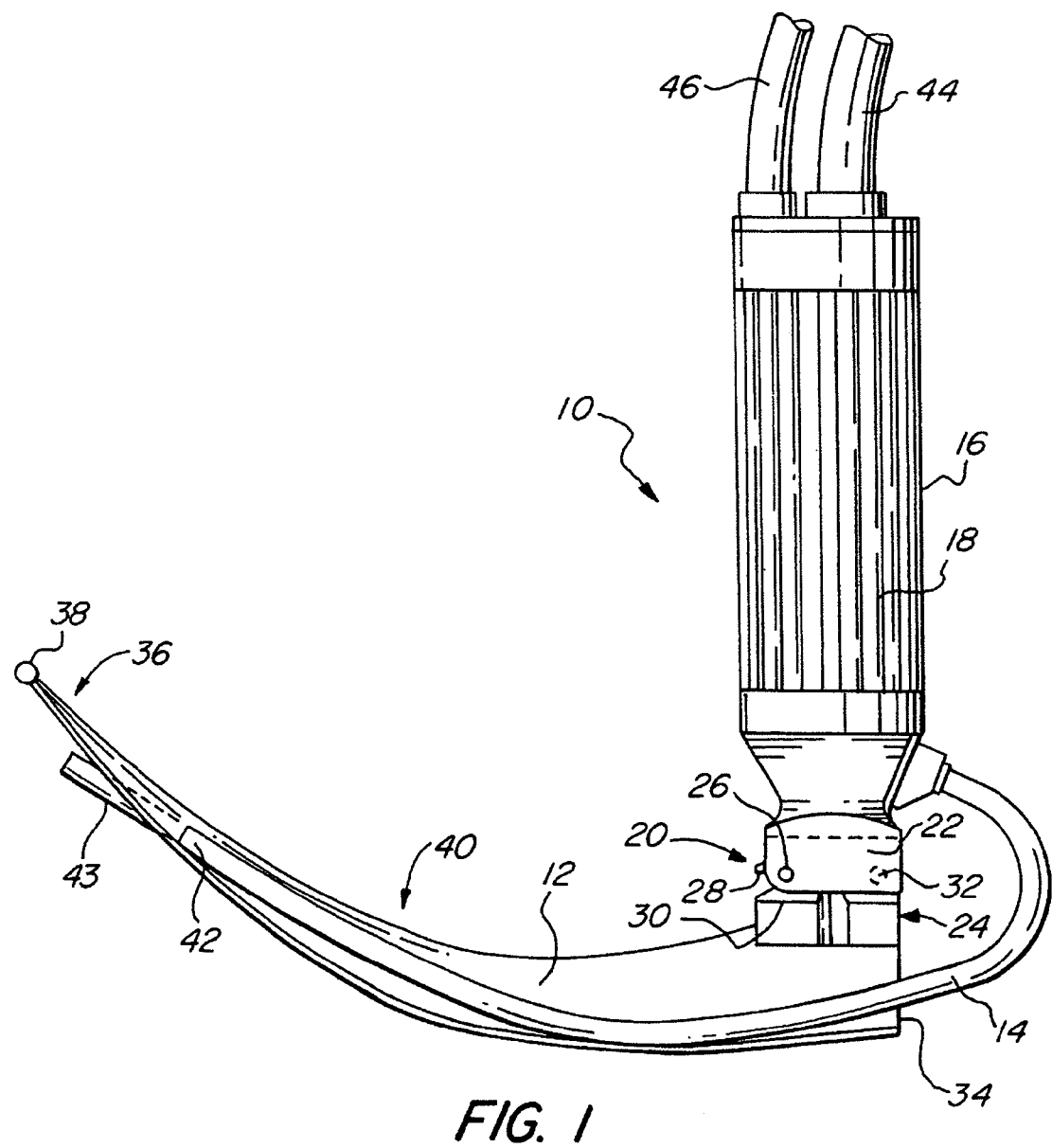
FIG. 1 is an illustration of the video laryngoscope with a curved blade and the light and image guide engaged with the handle.

The video laryngoscope 10, along with the attached blade 12 and light and image guide 14 is illustrated in FIG. 1.

The handle 16 is typically cylindrical with a knurled outer surface 18 thereby facilitating a secure gripping surface. As is shown in FIG. 1, the handle 16 is detachably joined to a blade 12, which in this instance is curved, by a hinge-type joinder 20.

The hinge-type joinder 20 includes a pair of conventional hinge socket 22 and connector 24 respectively mounted to the lower end of the handle 16 and to a proximal end 34 of the blade 12. Socket 22 further includes a crossbar 26. Connector 24 includes a hook 28 in a block 30 that fits into socket 22 and is more clearly seen in FIG. 2. The hook 28 engages the crossbar 26, and the handle 16 is rotated 90 degrees so that the blade will be rigidly held to the handle 16. This is a common hinge-type joinder 20 used in this type of instrumentation and is useful for all blade forms, of which the two illustrated forms are merely examples. A ball detent 32 detachably retains the handle 16 and blade 12 together and erect in the assembled configuration. The assembled instrument is rigid during the procedure.

Blade 12 has a distal end 36 which may be smoothed by a bulb-like edge 38. It has a curved top surface 40 extending from the distal end 38 toward the proximal end 34. This top surface 40 is used to elevate the tongue and permit the visualization of the vocal cords beneath it.

Referring back to FIGS. 1 and 2, blade 12 additionally includes an hole 42 at the distal end 36 of the blade 12. The hole 42 is designed to allow passage of a distal end 43 of light and image guide 14.

The handle is provided with means for obtaining an image of the field located beyond the tip of the blade 12, and for providing illuminating light to that field. In one embodiment, a camera (not shown) is mounted in a chamber inside the handle 16.

An image cable 44 to conduct image data from the camera exits from the top of the handle 16. It is connected to a video set (not shown), which provides data for an image on a video screen (not shown), for observation by the anesthesiologist. In addition, in some embodiments an illumination cable 46 conducts illuminating light to the handle 16.

In one embodiment, light for illumination of the field ahead of the distal end 36 of blade 12 is obtained from a separate light source (not shown) that can be placed in any convenient nearby location. An illumination cable 46, which may comprise a fiber optic bundle extends from the light source (not shown) to the handle 16. The illumination cable 46 need not be coherent, because it does not transmit an image—it transmits only illuminating light. Both the image cable 44 and the illumination cable 46 may enter the top of handle 16.

The actual construction of image cable 44 depends on the arrangement of the camera. In a preferred embodiment, the camera (not shown), customarily a COD chip, is mounted in the handle 16. In this case, the image cable 44 comprises a electrical cable, which extends from the camera output (not shown), out the top of the handle and to a video display (not shown). The image guide extending through the light and image guide 14, through the handle 16 and terminating at the camera input (not shown) comprises a bundle of coherent fiber optic cables to transmit the reflected light from the area ahead of the blade 12 to the camera (not shown).

In an alternative embodiment, the camera (not shown) may be located remotely from the video laryngoscope 10. In this case, the image guiding cable 44 would comprise a bundle of coherent fiber optic cables extending through the light and image guide 14, through the handle 16 and terminating at the camera, which is located remotely from the video laryngoscope 10.

Figure 3:
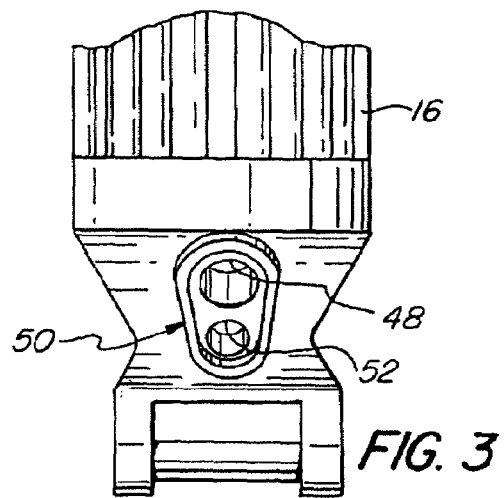
FIG. 3 is a perspective view of the handle depicting the housing containing the receptacles for the light and image guide.
Figure 4:
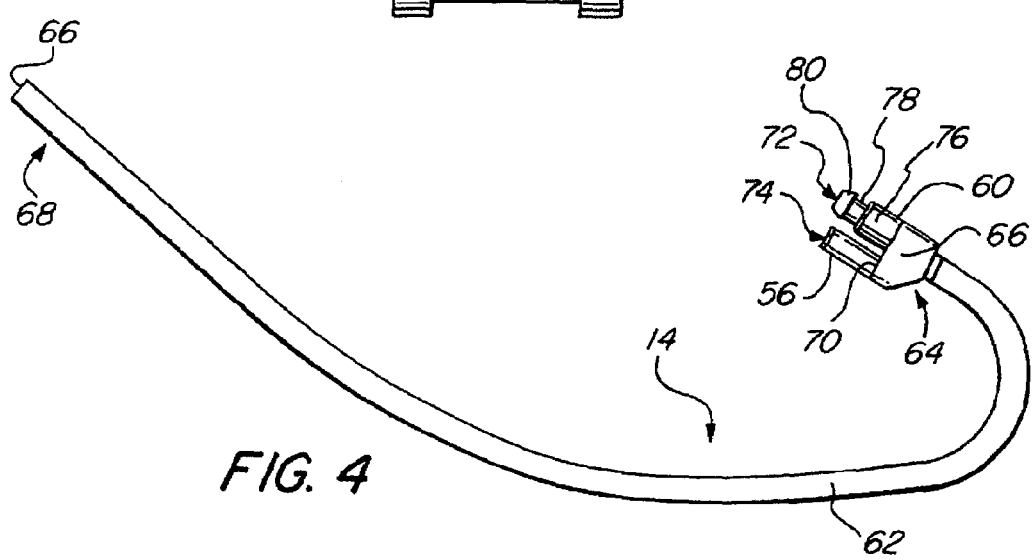
FIG. 4 is an illustration of the curved light and image guide as detached from the handle.
Figure 5:
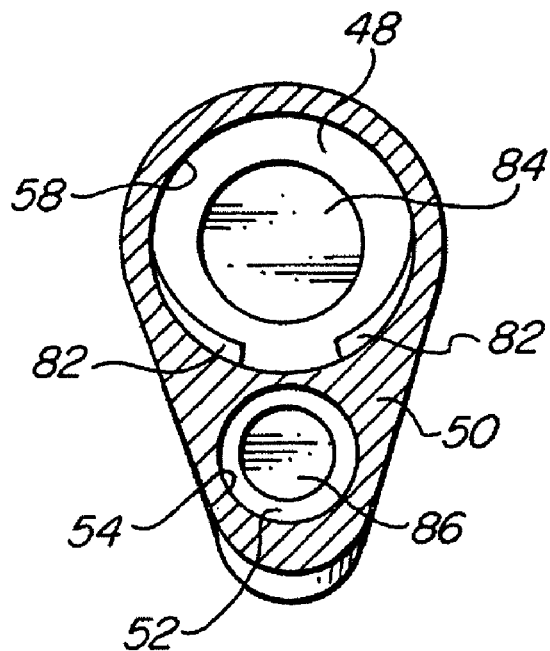
FIG. 5 is a cross-sectional view of the housing containing the receptacles for the light and image guide.
Figure 6:
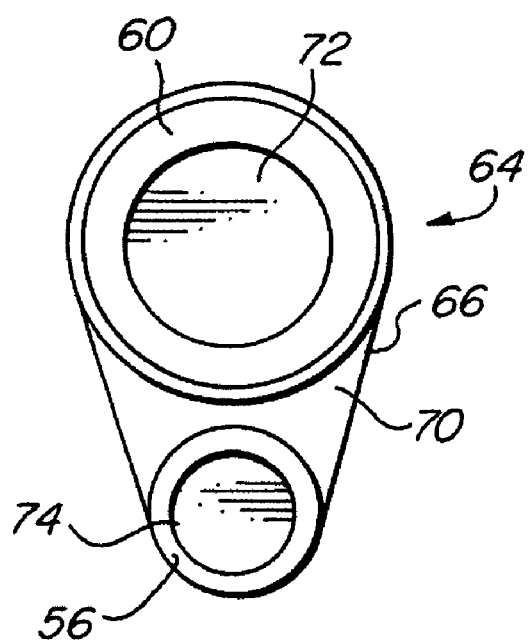
FIG. 6 is a cross-sectional view of the coupling element utilized in conjunction with the light and image guide.

The light guiding system receptacle 52 and the image guiding system receptacle 48 are both contained in housing 50 as illustrated in FIGS. 3 and 5. The light guiding system receptacle 52 has an inner surface 54 defining a cross-sectional diameter of the receptacle opening corresponding to a diameter of a first stem 56 shown in FIGS. 4, 5 and 6. Further, the image guiding system receptacle 48 has an inner surface 58 defining a cross-sectional diameter of the receptacle opening corresponding to a diameter of a second stem 60 also shown in FIGS. 4, 5 and 6.

FIG. 4 shows the light and image guide 14 detached from the handle 16. The light and image guide 14 may in one advantageous embodiment comprises a rigid curved shaft 62 and a coupling element 64. The coupling element 64 further comprises a first stem 56 and a second stem 60 along with a housing 66. The rigid curved shaft 62 is preferably made of stainless steel but may be manufactured on any rigid non-corroding material. The rigid curved shaft contains both, the light guiding cable 46 for transmitting illuminating light ahead of the distal end 36 of the blade 12, and the image guiding cable 44 for receiving the reflected light and transmitting it to the camera (not shown) located in the handle 16. The rigid curved shaft 62 also has a window 66, located at the distal end 68, which acts to seal the light and image guide 14. While it is contemplated that the light guiding cable 46 and the image guiding cable 44 are detachably connectable with the handle 16 via the coupling element 64, it is further contemplated that the light guiding cable 46 and the image guiding cable 44 associated with blade 40 may or may not be detachable from blade 40.

Referring back to the coupling element 64, an approximately cylindrical second stem 60, protrudes at one coupling end 70 of housing 66. The length and inside diameter of image guiding system receptacle 48 are selected so that second stem 60 can be received snugly therein. A window 72 is provided at the end of the second stem 60 to provide a seal for the image guiding cable 44. A first approximately cylindrical stem 56 extends from one coupling end 70 of housing 66 parallel to second stem 60. The first stem 56 is smaller in diameter and length than the second stem 60. Also window 74 is provided at the end of the first stem 56 to provide a seal for the light guiding cable 46.

Second stem 60, comprises a cylindrical segment 76, and annular groove 78, and a terminal conical segment 80. Both stems 56 and 60 extend in a coupling direction to mate with receptacles 52 and 48 respectively.

A locking element 82, displaceable radially with respect to the coupling direction, is located in housing 50. Locking element 82 may be approximately the shape of a two-tined fork that is bent inward in a circular shape at the outer end, the radius of curvature corresponding approximately to the radius of curvature of image guiding system receptacle 48. The outer ends of locking element 82 project slightly into image guiding system receptacle 48 as shown in FIG. 5.

Conical segment 80 of second stem 60 thereby encounters the ends of locking element 82 projecting into image guiding system receptacle 48 and displaces them radially outward.

When second stem 60 has been pushed into image guiding system receptacle 48 to the point that the ends of locking element 82 come to rest at the level of annular groove 78, they snap into annular groove 78.

In this position the coupling is now closed, i.e. coupling system 10 is coupled and mechanically interlocked. In this state, window 72 of second stem 60 and window 84 in the base of image guiding system receptacle 48 lie congruently with one another, thus creating an image-guiding coupling. Window 74 of first stem 56 comes to rest in front of window 86 of light guiding system receptacle 52, so that a light-guiding coupling is also created.

All that is necessary to release the coupling is withdraw the light and image guide 14 outward with enough force to overcome the locking element 82 as engaged in annular groove 78.

It is now seen that joining the blade 12, which may integrally include the light and image guide 14, to the handle 16 is a swift process. The portions of the joinder 20 are engaged and the handle 16 is then rotated, locking the blade 12 into place. The light and image guide 14 may further engage with coupling element 64 in a coupling direction.

Having a detachably connectable light and image guide 14 means that the light and image guide 14 may be detached from the handle 16 for sterilization. This further means that the handle 16 must no longer be hermetically sealed for sterilization. This provides the distinct advantage of lowering the cost involved with manufacturing the handle 16 as now they do not have to be subjected to the extremely high temperatures associated with the sterilization process. Further, any electronic components located in the handle 16 will no longer be subjected to the high temperatures of sterilization, which could prematurely age or damage them. While it is contemplated that light and image guide 14 is detachably connectable with the handle 16, it is further contemplated that light and image guide 14 associated with blade 40 may or may not be detachable from blade 40. It is further contemplated that while both light guiding system receptacle 52 and the image guiding system receptacle 48 are illustrated in the Figures as located on the side housing 50, it understood that the receptacles may be located at any convenient on housing 50 to match up with blade 40, such as for instance, when light and image guide 14 is provided integral with blade 40.

Instead of the camera and illumination arrangements already described, there are other alternatives, which can be used in any combination.

For example, instead of employing a separate light source (not shown), a battery and light bulb may be contained in the handle 16, and the light from this bulb focused onto light guiding cable 46. This eliminates the need for a fiber optic bundle from a light source, and also eliminates the separate light source itself.

Figure 7:
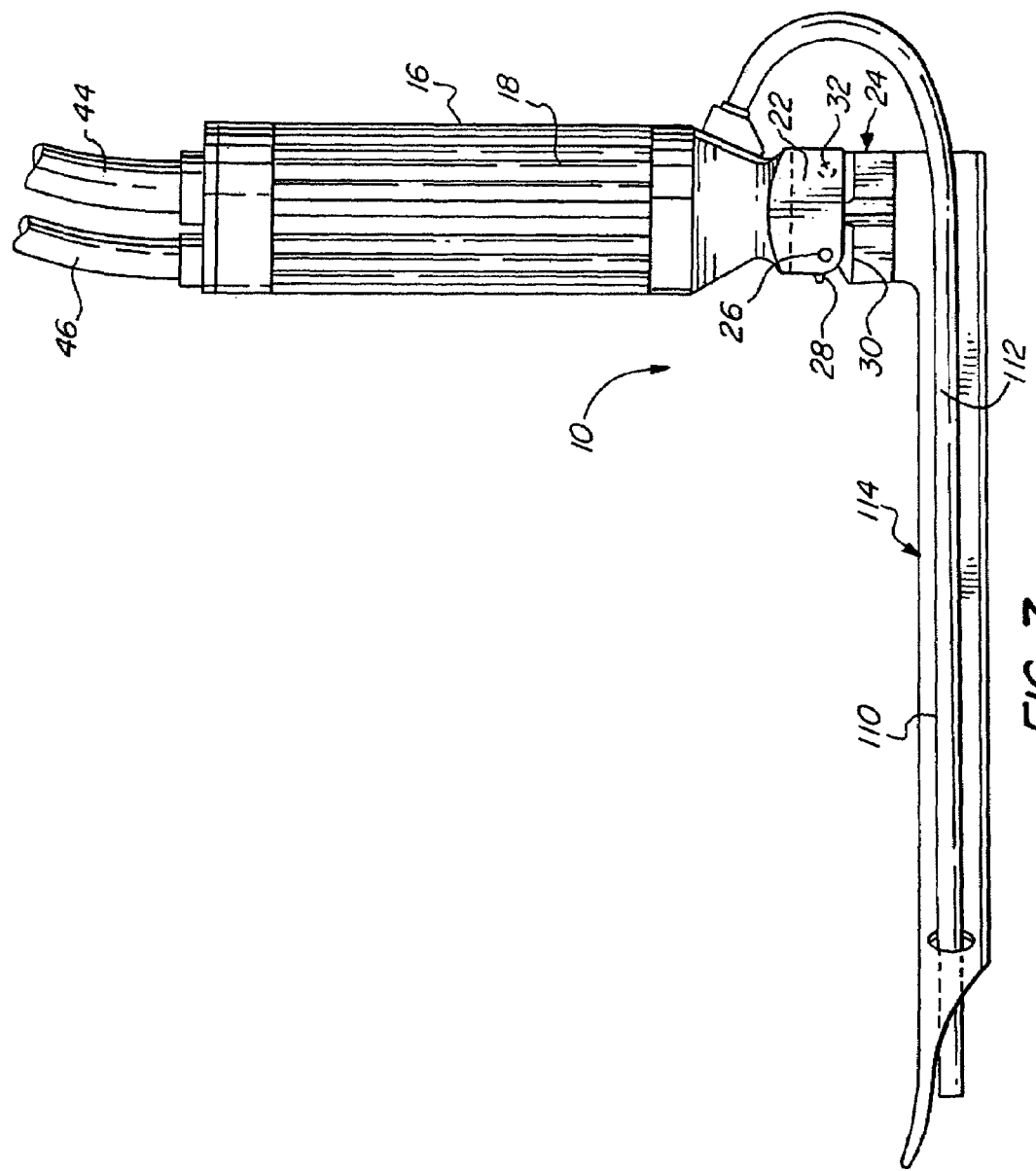
FIG. 7 is an illustration of the video laryngoscope with a straight blade and the light and image guide engaged with the handle.

The video laryngoscope 10, along with the attached blade 110 and light and image guide 112 is illustrated in FIG. 7.

Figure 2:
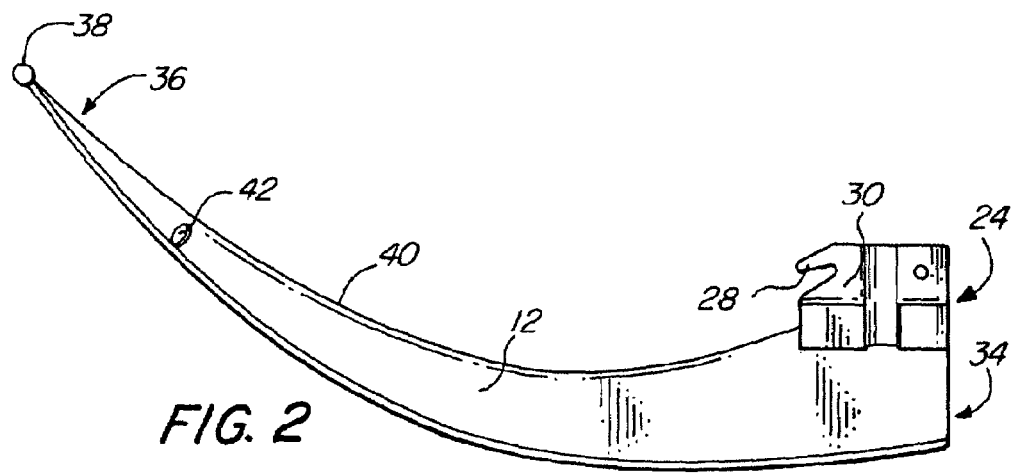
FIG. 2 is an illustration of a curved blade detached from the handle.

The blade 12 illustrated in FIGS. 1 and 2 is a curved blade 12, which is used to elevate the patients tongue in some circumstances. It is the well-known McIntosh blade 12. However, a different blade 110 for a different anatomical configuration is a straight blade 110 adapted for use in other circumstances. It is illustrated in FIG. 7. This is the well-known Foregger-Magill blade 110. These are the two most common blade shapes. Their configuration is not a limitation on the invention. The configurations of this handle 16 and these blades are completely conventional. They are standard equipment utilized by anesthesiologists trained to intubate the trachea. An advantage of this invention is that it does not require any additional training or re-training of anesthesiologists who have used these well known blades and will utilized them in the future.

The curved blade 12 illustrated in FIGS. 1 and 2 differs from the straight blade 110 illustrated in FIG. 7 only by its shape. The straight blade 110 in FIG. 7 has a straight upper surface 114 instead of a curved surface 40 for use when such a surface is preferred for lifting the tongue of the individual patient. In all cases the objective is to lift the tongue to permit visualization of the vocal cords and to enable the endotracheal tube to be accurately placed without harming surrounding tissue in the process.

In addition, the light and image guide 112 as shown in FIG. 7, differs from the light and image guide 14 as depicted in FIGS. 1 and 4 only by its shape. The light and image guide 14 is curved to match the curved blade 12 as depicted in FIGS. 1 and 4, whereas the light and image guide 112 is a straighter configuration corresponding to the straight blade 110 as shown in FIG. 7.

As the handle 16, the blade 110 and the light and image guide 112 operate in the same manner as the aforedescribed curved blade 12 and light and image guide 14, they will not be re-described.

Although the invention has been described with reference to a particular arrangement of parts, features and the like, these are not intended to exhaust all possible arrangements or features, and indeed many other modifications and variations will be ascertainable to those of skill in the art.

The invention claimed is:

1. A video laryngoscope comprising:
   a handle including a first light guide and a first image guide;
   a first connector associated with said handle, said first connector terminating the first light guide and the first image guide;
   a blade coupled to one end of said handle, said blade including a second light guide and a second image guide;
   a second connector associated with said blade, said second connector terminating the second light guide and the second image guide;
   said first connector being engageable with said second connector such that the first light guide and the first image guide are in communication with the second light guide and the second image guide respectively, when said first connector is engaged with said second connector.

2. The video laryngoscope according to claim 1 further comprising a light source for generating illuminating light and a camera for generating an image signal.

3. The video laryngoscope according to claim 2 wherein said illuminating light is transmitted to an area ahead of said blade via the first and second light guide.

4. The video laryngoscope according to claim 3 wherein reflected light from the area ahead of said blade is transmitted back to said camera via the first and second image guides.

5. The video laryngoscope according to claim 4 wherein said camera generates the image signal based on the reflected light received via the first and second image guides.

6. The video laryngoscope according to claim 2 further comprising a video screen coupled to said camera.

7. The video laryngoscope according to claim 6 wherein said video screen receives the image signal generated by said camera and displays a visual representation of the area ahead of said blade.

8. The video laryngoscope according to claim 2 wherein said camera is positioned within said handle.

9. The video laryngoscope according to claim 1 wherein said light source is positioned within said handle.

10. The video laryngoscope according to claim 1 further comprising a source of electrical power for powering said light source.

11. The video laryngoscope according to claim 10 wherein said source of electrical power is positioned within said handle.

12. The video laryngoscope according to claim 1 wherein said blade is disposable.

13. The video laryngoscope according to claim 1 further comprising a locking element for securing said blade to said handle.

14. The video laryngoscope according to claim 1 wherein said second light guide and said second image guide are non-removably positioned within said blade.

15. A method for displaying an image representative of an area ahead of a laryngoscope comprising the steps of:
   positioning a first light guide and a first image guide within a handle;
   terminating the first light guide and the first image guide in a first connector that is associated with the handle;
   positioning a second light guide and a second image guide within a blade;
   terminating the second light guide and the second image guide in a second connector that is associated with the blade;
   attaching the blade to the handle;
   coupling the first light guide and the first image guide to the second light guide and the second image guide respectively via the first and second connectors;
   transmitting illuminating light via the first and second light guides to an area ahead of the blade;
   transmitting reflected light via the first and second image guides to a camera positioned in the handle;
   generating a video image of representative of the received reflected light;
   displaying the video image on a video screen.

* * * * *